United States Patent
King et al.

(10) Patent No.: US 7,923,020 B2
(45) Date of Patent: Apr. 12, 2011

(54) COMPOSITE FOR IMPLANTATION IN THE BODY OF AN ANIMAL AND METHOD FOR MAKING THE SAME

(75) Inventors: Richard S. King, Warsaw, IN (US); Mark D. Hanes, Winona Lake, IN (US); Luke Aram, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 276 days.

(21) Appl. No.: 11/540,616

(22) Filed: Sep. 29, 2006

(65) Prior Publication Data

US 2008/0081061 A1 Apr. 3, 2008

(51) Int. Cl.
*A61F 2/00* (2006.01)
(52) U.S. Cl. ........................................ 424/423
(58) Field of Classification Search ............... None
See application file for complete search history.

(56) References Cited

U.S. PATENT DOCUMENTS

| | | | |
|---|---|---|---|
| 4,187,210 A * | 2/1980 | Howard, Jr. | 524/730 |
| 4,202,055 A | 5/1980 | Reiner et al. | |
| 4,373,217 A | 2/1983 | Draenert | |
| 4,451,235 A * | 5/1984 | Okuda et al. | 433/201.1 |
| 4,609,527 A * | 9/1986 | Rinderle et al. | 419/32 |
| 4,629,464 A * | 12/1986 | Takata et al. | 623/23.61 |
| 4,781,183 A | 11/1988 | Casey et al. | |
| 5,210,130 A * | 5/1993 | Howard, Jr. | 524/789 |
| 5,348,760 A * | 9/1994 | Parker et al. | 427/9 |
| 5,650,108 A * | 7/1997 | Nies et al. | 264/122 |
| 6,558,794 B1 | 5/2003 | Fehrenbacher et al. | |
| 6,869,445 B1 * | 3/2005 | Johnson | 623/17.11 |
| 2003/0206928 A1 | 11/2003 | Tormala et al. | |
| 2007/0059334 A1 * | 3/2007 | Abt et al. | 424/423 |

FOREIGN PATENT DOCUMENTS

EP 0339816 11/1989
WO WO 03026714 A1 * 4/2003

* cited by examiner

*Primary Examiner* — Michael G Hartley
*Assistant Examiner* — Paul Dickinson
(74) *Attorney, Agent, or Firm* — Barnes & Thornburg LLP (57) ABSTRACT

Composites that include a ceramic substance disposed in a polymeric material and associated methods for making the same.

14 Claims, 5 Drawing Sheets

COMPOSITE FOR IMPLANTATION IN THE BODY OF AN ANIMAL AND METHOD FOR MAKING THE SAME

BACKGROUND

The joints of a human body are subject to substantial stresses, and as people age, one or more components of a joint may function less effectively than when they were younger. Injury and disease can also adversely affect the function of joint components. Accordingly, it is increasingly common to replace natural joint components, or an entire joint, with prosthetic ones when the natural joints wear out or no longer function properly. Examples of natural joints being repaired or replaced with prosthetic components include hip, knee, elbow, and shoulder joints.

The implant materials used to fabricate prosthetic components need to possess certain mechanical and chemical properties in order to function and exist in contact with the biological tissue of a living organism. For example, these materials should possess the appropriate mechanical/chemical properties so they do not induce undesirable reactions in the body such as blood clotting, tissue death, tumor formation, allergic reaction, foreign body reaction (rejection), and/or inflammatory reaction. In addition, these materials should posses the appropriate strength, elasticity, permeability, and flexibility in order for the prosthetic component to function properly. Moreover, it is desirable that these materials (i) sterilize easily and (ii) substantially maintain their physical properties during the time the prosthetic component remains in contact with the biological tissue. Various polymeric materials satisfy one or more of the above discussed mechanical/chemical properties.

Accordingly, a number of prosthetic components for implantation in the body of an animal are constructed from, or include, a polymeric material. Therefore, enhancing or improving one or more characteristics of a polymeric material for use in a prosthetic implant is desirable.

SUMMARY

A medical apparatus, for example an orthopedic device or a component thereof, for implanting into a body of an animal, and a method for preparing the same, in accordance with the present disclosure comprises one or more of the following features or combinations thereof:

A substance for implanting into the body of an animal, comprising a composite that includes a ceramic substance disposed in a biocompatible polymeric material. The ceramic substance may be dispersed throughout the polymeric material as discrete ceramic units such as particles, fibers, and/or whiskers. The ceramic units may be enclosed by the polymeric material. The ceramic substance may be substantially evenly dispersed throughout the polymeric material. Note that in one embodiment the weight and/or volume percent of the ceramic material is less than that of the polymeric material weight and/or volume percent.

The ceramic substance may include one or more of the following, oxides, nitrides, borides, carbides, silicides, sulfides, aluminides, berylides, phosphides, antimonides, and arsenides. The ceramic substance may also comprise one or more of the following, hydroxyapatite, calcium phosphate, calcium carbonate, calcium sulfate, bioglass, zirconium oxide, barium sulfate, and titanium oxide. The biocompatible polymer may include one or more of the following, polyesters, poly(methylmethacrylate), nylon, polycarbonates, polyethylene copolymers, grafted polyethylene matrix and polyolefins. Furthermore the biocompatible polymer may include one or more of the following, methyl methacrylate, methyl acrylate, ethyl methacrylate, ethyl acrylate, and butyl methacrylate. The biocompatible polymer may include one or more of the following, high density polyethylene, high molecular weight polyethylene, high density high molecular weight polyethylene. In one embodiment the biocompatible polymer includes UHMWPE.

As indicated above, the ceramic substance may take any physical form e.g. the physical form of one or more of the following, ceramic particles, ceramic fibers, and/or ceramic whiskers. The ceramic substance may be surrounded by the polymer. For example, ceramic particles, ceramic fibers, and/or ceramic whiskers may be contained or enclosed within the polymer. Ceramic particles may be nanoparticles and/or microparticles. The ceramic substance can be coated with a polymeric material. The coating may be different from the biocompatible polymer. The polymeric material may comprise one or more of the following, poly(vinyl alcohol) and polyethylene copolymers.

The substance for implanting into the body of an animal may include ceramic free polymeric material attached to the composite. The substance may also include the ceramic free polymer integrally attached to the composite. In addition the substance may include a composite configured as a tray of an implantable orthopedic device. The substance may also include a composite configured as a shell of modular implantable orthopedic device.

The composite may be utilized in an arrangement for implanting into the body of an animal. The arrangement may be, or include, an orthopedic device having a component. The component may include a composite made from discrete units of a ceramic substance disposed in a biocompatible polymeric material. The composite may include hydroxyapatite particles while the biocompatible polymeric material includes UHMWPE. In one embodiment the hydroxyapatite particles are coated with a polymeric material other than UHMWPE. For example, the polymeric material may include poly(vinyl alcohol). In one embodiment the composite includes particles of a ceramic substance disposed in crosslinked UHMWPE.

Methods for making composites of the present disclosure are described below. It should be understood that any appropriate combination of ceramic particles (coated or uncoated) and polymeric particles may be utilized in fabricating the composite. One method of making a composite of the present disclosure may include:
  (i) mixing ceramic particles with polymer particles to obtain a ceramic particle/polymer particle blend, and
  (ii) subjecting the blend to compression molding to obtain a composite.

In addition to compression molding, the above method can also include subjecting the blend to a radiation treatment (crosslinking) and/or a melt annealing regimen to obtain a composite. Note that a thin polymer layer may be molded on to the composite to shield it from abrasion potentially caused by loosened ceramic particles.

Another illustrative method of making a hydroxyapatite/ultrahigh molecular weight polyethylene composite of the present disclosure may include:
  (i) mixing hydroxyapatite (HA) particles with ultrahigh molecular weight polyethylene (UHMWPE) particles to make a HA particle/UHMWPE particle blend (the blend), and
  (ii) subjecting the blend to compression molding to obtain a composite.

As stated before, in addition to compression molding, the above method can also include subjecting the blend to a radiation treatment (crosslinking) and/or a melt annealing regimen to obtain a composite. In one embodiment, HA content is 46% by weight and 21% by volume as compared to the polymeric material.

Composites can also be made utilizing ceramic particles pre-coated with a polymer, or a functional monomer, prior to blending with polymer particles. As indicated above, polymers used for pre-coating may include poly(vinyl alcohol) and polyethylene copolymers, such as poly(vinyl alcohol-co-ethylene). Cold-water soluble grade of poly(vinyl alcohol) can be utilized. For example, a cold-water soluble grade with degree of hydrolysis between about 75% to about 80% and a molecular weight between about 1,000 to about 10,000 daltons may be utilized. Hot-water soluble grade of poly(vinyl alcohol) may also be used. For example, a hot-water soluble grade between about 85% to about 99% degree of hydrolysis and molecular weight between about 10,000 to about 200,000 daltons may be used. When utilizing cold-water soluble grade of poly(vinyl alcohol) polymers the concentration for coating can vary from about 2% to about 20%. With hot-water soluble poly(vinyl alcohol) polymers the concentration may vary from about 2% to about 5%. For preparation of poly(vinyl alcohol-co-ethylene) coating solution, either dimethyl sulfoxide (DMSO) or a mixture of 50/50 water/n-propanol can be used.

Examples of functional monomers include fumaric acid and itaconic acid. Radiation crosslinking may be used when a functional monomer is used as a coating. An illustrative method of making a composite using poly(vinyl alcohol) coated ceramic particles and UHMWPE may include:

(i) making a solution of Poly(vinyl alcohol) (PVA),
(ii) placing HA particles into the PVA solution to obtain a PVA/HA slurry,
(iii) drying the PVA/HA slurry to obtain PVA coated HA particles,
(iv) mixing the dried PVA coated HA particles with UHMWPE particles to make a PVA coated HA particle/UHMWPE particle blend (the blend), and
(v) subjecting the blend to compression molding to obtain a composite.

The above method can also include radiation treatment and/or a melt annealing regimen to obtain a composite. Note that using polymer coated ceramic particles in making a composite enhances the dispersion in and adhesion between the polymer and the ceramic particles. In addition, using coated ceramic particles inhibits agglomeration of the ceramic particles during the process. Moreover, utilizing coated ceramic particles allows crosslinking between the polymer the particles are disposed in and the coating. This crosslinking enhances incorporation of the particles into the polymer. In addition, coating of the ceramic particles enhances the biocompatibility of the composite.

A method for preparing a component that includes a polymer layer attached to a composite layer may include the following:

(i) providing a polymeric preform,
(ii) placing a blend of polymeric particles and ceramic particles in contact with the polymeric perform, and
(iii) subjecting the polymeric perform and the blend of ceramic and polymeric particles to compression molding to obtain a component having a polymer layer attached to a composite layer.

If a crosslinked polymer layer is desired the above method can also include vacuum foil packaging the polymeric perform and then irradiating (e.g. gamma rays) the polymeric perform in a well known manner to cause crosslinking. Once crosslinking is finished then the blend of ceramic and polymeric particles are placed in contact with the crosslinked polymeric perform and subjected to compression molding. Note that residual free radicals generated during the irradiation step are quenched during the consolidation of the polymer layer to the composite layer. Also note that any of the above methods may include sterilizing the component and/or composite.

Additional features of the present disclosure will become apparent to those skilled in the art upon consideration of the following detailed description of preferred embodiments exemplifying the best mode of carrying out the subject matter of the disclosure as presently perceived.

DESCRIPTION

While the disclosure is susceptible to various modifications and alternative forms, specific embodiments will herein be described in detail. It should be understood, however, that there is no intent to limit the disclosure to the particular forms described, but on the contrary, the intention is to cover all modifications, equivalents, and alternatives falling within the spirit and scope of the disclosure.

The present disclosure generally relates to a medical apparatus. This disclosure also relates to an implantable orthopedic device. The present disclosure further relates to an implantable biocompatible composite and associated methods for making the same. An implantable biocompatible composite of the present disclosure will hereafter be referred to as a composite. These composites described herein include a ceramic substance disposed in a polymeric material. A composite of the present disclosure will possess characteristics which allow it to be implanted into the body of an animal (e.g. a human). For example, a composite will possess mechanical and chemical properties in order to function and exist in contact with the biological tissue of an animal. For example, the composite will possess the appropriate properties so it does not induce undesirable reactions in the body such as blood clotting, tissue death, tumor formation, allergic reaction, foreign body reaction (rejection), and/or inflammatory reaction. In addition, the composite will posses the appropriate strength, elasticity, permeability, and flexibility in order for it to function properly for its intended purpose. Moreover, it is desirable that the composites (i) sterilize easily and (ii) substantially maintain their physical properties during the time it remains in contact with biological tissue.

A biocompatible "ceramic substance" or "ceramic" as used herein means inorganic, nonmetallic matter. A ceramic substance may include one or more of the following: oxides, nitrides, borides, carbides, silicides, and/or sulfides. Intermetallic compounds such as aluminides and berylides are also considered ceramics as are phosphides, antimonides, and arsenides. Furthermore, the ceramic may contain glass or be substantially free of glass. Examples of ceramics which can be utilized in the composite include hydroxyapatite, calcium phosphate, calcium carbonate, calcium sulfate, bioglass, zirconium oxide, barium sulfate, and titanium oxide. The ceramic substance may be resorbable. In addition, the ceramic substance may be configured in any form appropriate for utilization in the composite. For example, the ceramic substances make take the form of nanoparticles, microparticles, whiskers or fibers.

What is meant herein by a biocompatible "polymeric material" or "polymer" is any medical grade polymeric material which may be implanted into an animal (e.g. a human patient). Polymers include, but are not limited to, polyesters, poly(methylmethacrylate), nylon, polycarbonates, polyethylene copolymers, grafted polyethylene matrix and polyolefins. The term "polymer" is also intended to include both homopolymers and copolymers; thus, "polymer" includes a copolymer comprising ethylene and an acrylate derivative, such as methyl methacrylate, methyl acrylate, ethyl methacrylate, ethyl acrylate, and butyl methacrylate.

An example of a polymer substance is medical grade polyethylene. The term "polyethylene" includes polyethylene, such as a polyethylene homopolymer, high density polyethylene, high molecular weight polyethylene, high density high molecular weight polyethylene, or any other type of polyethylene utilized in the construction of a prosthetic device. A more specific example of such a polymer is medical grade ultrahigh molecular weight polyethylene (UHMWPE).

Figure 5:
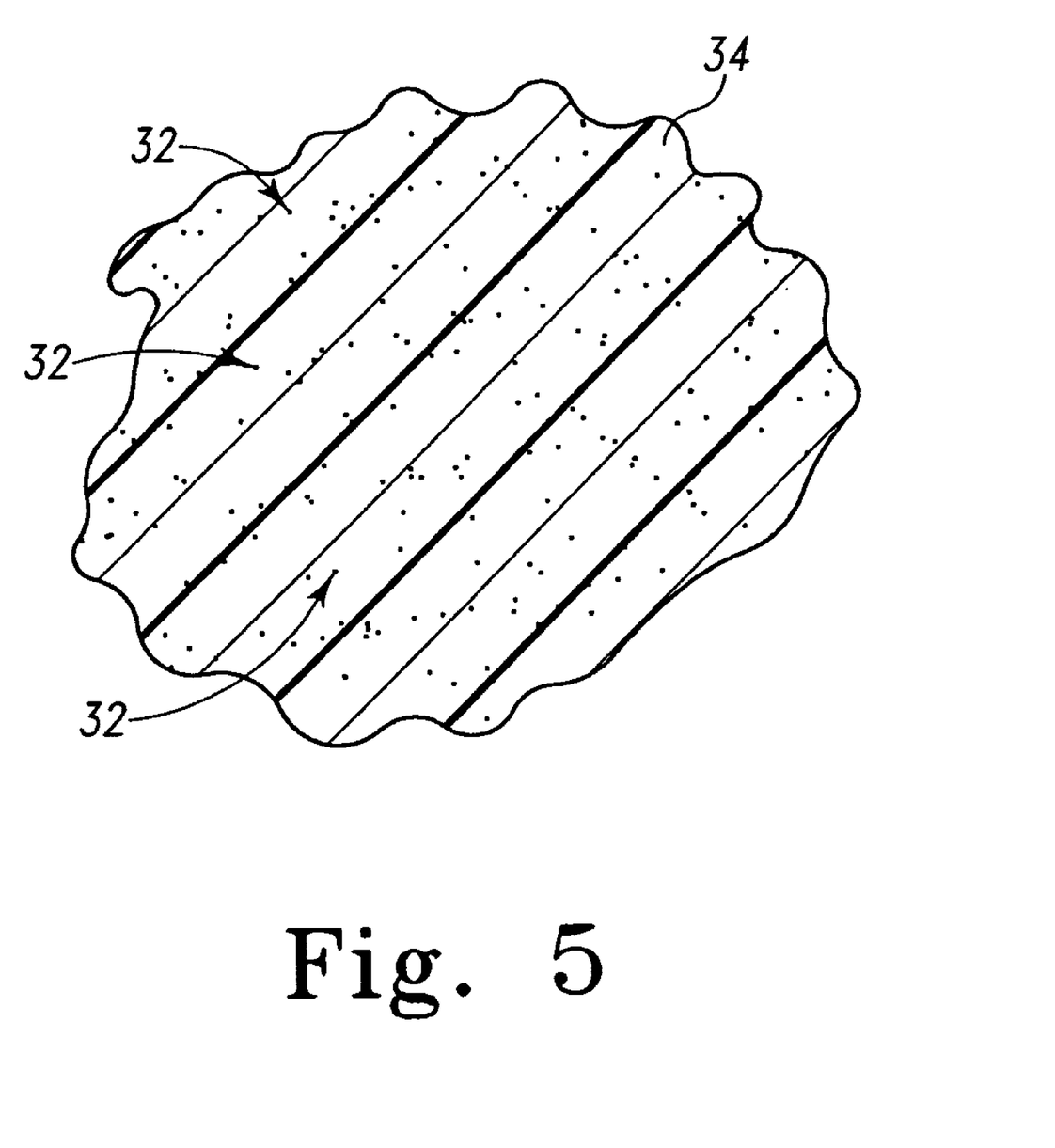
FIG. 5 depicts a ceramic substance dispersed in a polymeric material.

As discussed in greater detail below, the composites described herein include a ceramic substance 32 (in this embodiment particles) dispersed in a polymeric material 34 as depicted in FIG. 5.

The composite may be utilized in a number of joint replacement or repair procedures, such as surgical procedures associated with the hip, shoulders, knees, ankles, knuckles, or any other joint. For example, the composite may be used in the fabrication of prosthetic devices for implantation into the body of a patient. Illustrative examples of prosthetic devices of the present disclosure include those configured for implantation into a glenoid of a patient, an acetabulum of a patient, or tibia of a patient. In one embodiment the composite may be utilized in the fabrication of one or more components of a prosthetic device. The composite may also be used as an integral part or layer of a polymer prosthetic component or device. The composite may be used as a backside section in contact with a metal shell or a metal tray in a modular prosthetic device implant system. In addition, the composite may be utilized as a tray or shell in a non-articulating part of a prosthetic device, while the articular surface is made from a polymer. The articular serves as an articulating or bearing surface on which either a natural bone structure or a prosthetic component articulates. In addition, a composite may be utilized to fabricate an engaging surface. The engaging surface may include locking features in the form of mechanisms such as pins, tabs, tapered posts, or the like for locking or otherwise securing a component to either another component associated with a prosthetic device (e.g., a metal shell or tray) or to the bone itself.

Methods for making composites of the present disclosure are described below. It should be understood that any appropriate combination of ceramic particles (coated or uncoated) and polymeric particles may be utilized in fabricating the composite. The phrase "ceramic particles" includes nanoparticles, microparticles, whiskers, fibers, or any other physical form, or combination of forms, compatible with the present disclosure. Furthermore, the phrase "polymer particles" includes any physical polymeric form (e.g. flakes, fibers, whiskers), or combination of forms, compatible with the present disclosure. One method of making a composite of the present disclosure may include:

(i) mixing ceramic particles with polymer particles to obtain a ceramic particle/polymer particle blend, and
(ii) subjecting the blend to compression molding to obtain a composite.

In addition to compression molding, the above method can also include subjecting the blend to a radiation treatment (crosslinking) and/or a melt annealing regimen to obtain a composite. Note that a thin polymer layer may be molded on to the composite to shield it from abrasion potentially caused by loosened ceramic particles.

An illustrative method of making a hydroxyapatite/ultrahigh molecular weight polyethylene composite of the present disclosure may include:

(i) mixing hydroxyapatite (HA) particles with ultrahigh molecular weight polyethylene (UHMWPE) particles to make a HA particle/UHMWPE particle blend (the blend), and
(ii) subjecting the blend to compression molding to obtain a composite.

As stated before, in addition to compression molding, the above method can also include subjecting the blend to a radiation treatment (crosslinking) and/or a melt annealing regimen to obtain a composite. Note that in one embodiment the HA content was 46% by weight and 21% by volume.

Composites can also be made utilizing ceramic particles pre-coated with a polymer, or a functional monomer, prior to blending with polymer particles. Polymers used for pre-coating include poly(vinyl alcohol) and polyethylene copolymers, such as poly(vinyl alcohol-co-ethylene). Cold-water soluble grade of poly(vinyl alcohol) can be utilized. For example, a cold-water soluble grade with degree of hydrolysis between about 75% to about 80% and a molecular weight between about 1,000 to about 10,000 daltons may be utilized. Hot-water soluble grade of poly(vinyl alcohol) may also be used. For example, a hot-water soluble grade between about 85% to about 99% degree of hydrolysis and molecular weight between about 10,000 to about 200,000 daltons may be used. When utilizing cold-water soluble grade of poly(vinyl alcohol) polymers the concentration for coating can vary from about 2% to about 20%. With hot-water soluble poly(vinyl alcohol) polymers the concentration may vary from about 2% to about 5%. For preparation of poly(vinyl alcohol-co-ethylene) coating solution, either dimethyl sulfoxide (DMSO) or a mixture of 50/50 water/n-propanol can be used.

Examples of functional monomers include fumaric acid and itaconic acid. Radiation crosslinking may be used when a functional monomer is used as a coating. An illustrative method of making a composite using poly(vinyl alcohol) coated ceramic particles and UHMWPE may include:

(i) making a solution of Poly(vinyl alcohol) (PVA),
(ii) placing HA particles into the PVA solution to obtain a PVA/HA slurry,
(iii) drying the PVA/HA slurry to obtain PVA coated HA particles,
(iv) mixing the dried PVA coated HA particles with UHMWPE particles to make a PVA coated HA particle/UHMWPE particle blend (the blend), and
(v) subjecting the blend to compression molding to obtain a composite.

The above method can also include radiation treatment and/or a melt annealing regimen to obtain a composite. Note that using polymer coated ceramic particles in making a composite enhances the dispersion in and adhesion between the polymer and the ceramic particles. In addition, using coated ceramic particles inhibits agglomeration of the ceramic particles during the process. Moreover, utilizing coated ceramic particles allows crosslinking between the polymer and the coated particles. This crosslinking enhances incorporation of the particles into the polymer. In addition, coating of the ceramic particles enhances the biocompatibility of the composite.

A method for preparing a component that includes a polymer layer attached to a composite layer may include the following:

(i) providing a polymeric preform,
(ii) placing a blend of polymeric particles and ceramic particles in contact with the polymeric perform, and
(iii) subjecting the polymeric perform and the blend of ceramic and polymeric particles to compression molding to obtain a component having a polymer layer attached to a composite layer.

If a crosslinked polymer layer is desired the above method can also include vacuum foil packaging the polymeric perform and then irradiating (e.g. gamma rays) the polymeric perform in a well known manner to cause crosslinking. Once crosslinking is finished then the blend of ceramic and polymeric particles are placed in contact with the crosslinked polymeric perform and subjected to compression molding. Note that residual free radicals generated during the irradiation step are quenched during the consolidation of the polymer layer to the composite layer. Also note that any of the above methods may include sterilizing the component and/or composite.

It should be appreciated that using compression molding results in a one step formation of any composite and any combination of a composite layer with a polymer layer. It should also be appreciated that in a combination of a composite layer with a polymer layer, either layer or both layers may be crosslinked.

Now turning to the physical/chemical characteristics of a composite of the present disclosure. Recall that a composite will possess mechanical and chemical properties in order to function and exist in contact with the biological tissue of an animal. For example, a composite will possess the appropriate properties so it does not induce undesirable reactions in the body such as blood clotting, tissue death, tumor formation, allergic reaction, foreign body reaction (rejection), and/or inflammatory reaction. In addition, a composite will posses the appropriate strength, elasticity, permeability, and flexibility in order for it to function properly for its intended purpose. Moreover, it is desirable that composites (i) sterilize easily and (ii) substantially maintain their physical properties during the time it remains in contact with biological tissue. The particular desired characteristics of a composite typically depends upon the function the composite serves, since different functions may have different requirements.

One way of producing a composite with the desired characteristics is to manipulate (i) the materials used to fabricate a composite and/or (ii) the fabrication conditions. Examples of manipulating the materials include one or more of the following (i) the chemical composition of the ceramic particles/polymer particles used to make a blend, (ii) the material used to coat the ceramic particles if coated particles are desired (iii) the ratio of coated and/or uncoated ceramic particles to polymer particles, (iv) the type of functional monomer used to coat the ceramic particles if coated particles are desired, and (v) degree of crosslinking. Examples of manipulating the fabrication conditions include one or more of the following (i) conditions used in coating ceramic particles, (ii) conditions for compression molding (consolidating) the ceramic particles (coated or uncoated) with the polymer particles to make a composite, (iii) conditions for attaching a composite layer to a polymeric layer (integral or otherwise), (iv) conditions for crosslinking, (v) conditions for annealing, and (vi) conditions for sterilizing a composite or a device containing a composite. Any one of the above, or other factors, or combination of the above or other factors, can be manipulated to obtain a composite with the desired characteristics. In addition, the manipulation required to obtain a composite with desirable characteristics can be determined by routine experimentation.

One reason why using a composite in a prosthetic component is desirable is that typically a bone or a metallic component of a prosthetic device (e.g. backside or tray) has a higher elastic modulus as compared to polymers such as UHMWPE. For example, UHMWPE and PMMA have elastic moduli of 100 ksi and 345 ksi, respectively. Cortical bone, titanium and cobalt-chromium alloy have elastic moduli of 2100 ksi, 17,000 ksi and 30,000 ksi, respectively. Accordingly, when a polymer portion of a prosthetic device is attached to a metallic component or a bone by a mechanical mechanism or by cement, this gap in elastic modulus tends to cause the polymeric portion to loosen from the metallic component, cement or bone. It should be appreciated that a common characteristic shared by the composites of the present disclosure is that they all have a greater elastic modulus as compared to the polymer (conventional or crosslinked) prior to adding the ceramic particles. This increase in elastic modulus decreases the aforementioned elastic modulus gap. The decrease in the elastic modulus gap inhibits loosening and creep tendency, while enhancing fixation and dimensional stability for a snug snap-fit. Thus it should be appreciated that a composite component is less likely to loosen from a metallic component or a bone as compared to a polymer component. For example, using a composite tray will inhibit the loosening of the tray from the bone as compared to using a polymer tray. In addition, a composite attached to a metallic component is less likely to loosen as compared to a polymer component attached to a metallic component. Moreover, when cement is utilized to fix a composite to a bone or another component the composite has a high enough elastic modulus so as to decrease the amount of stress transmitted to the cement. Accordingly, using a composite in combination with cement helps maintain the integrity of the cement and enhances its ability to maintain fixation. Furthermore, the elastic modulus of composites are high enough they can substitute for metallic components. The composites are less expensive as compared to metallic ones. Accordingly, the expense of manufacturing prosthetic devices decreases when composites are used instead of metallic ones. In addition, disposing ceramic substances (e.g. particles) in a polymer may improve the polymer's radiopacity.

Figure 1:
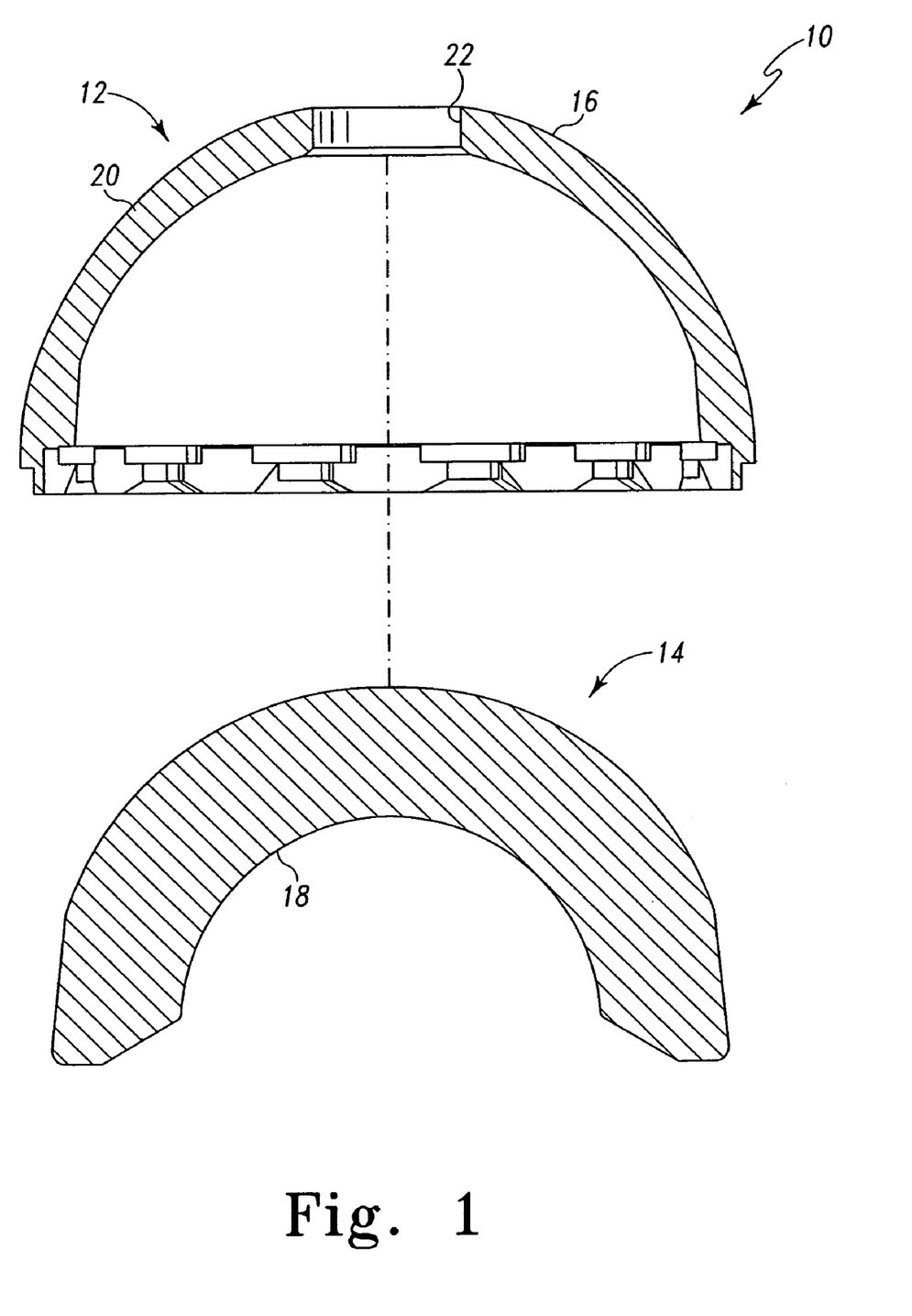
FIG. 1 is an illustration of a modular prosthetic device system.

Specific examples of how a composite of the present disclosure may be used as a prosthetic component are discussed below. For example, the composite may serve as a shell in a modular prosthetic device system, or a backside or tray in a prosthetic device. In particular, FIG. 1 illustrates a portion of a modular prosthetic device system 10. The system includes a shell 12 and a polymeric liner 14. In this embodiment the shell 12 is made of a composite 20 of the present disclosure and is configured to accept the liner 14. In addition, the shell 12 has a fixation surface 16 defined thereon. The liner 14 has a polymeric bearing or articulating surface 18 defined thereon. The articulating surface 18 serves as a surface for an anatomical structure, or a prosthetic component, to articulate upon. Having polymeric articulating surface 18 maintains the advantages of using a polymer for a articulating or bearing surface. A bone (not shown), or other anatomical structure, may be secured to the fixation surface 16 via one or more screws (see screw hole 22) or via a cement. The liner 14 can be attached to the shell in any number of well known techniques, e.g. snap or press fit.

Figure 2:
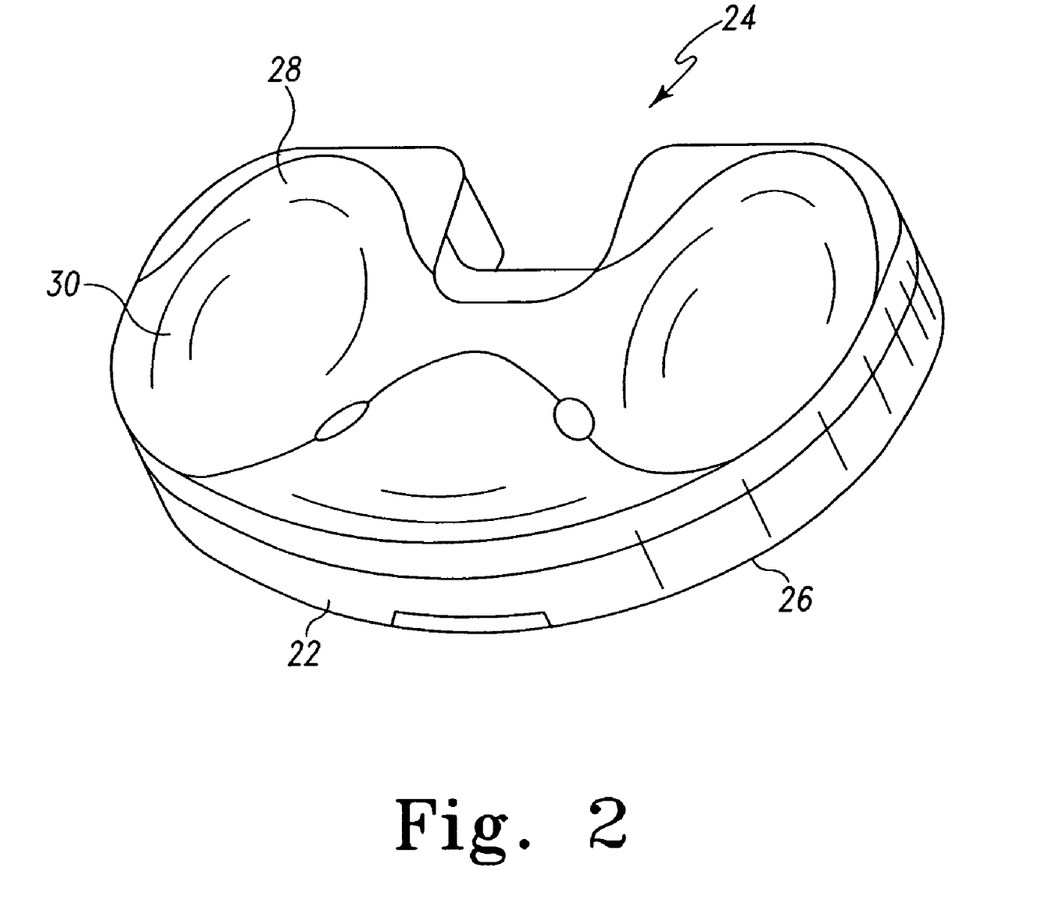
FIG. 2 is an illustration of a tibial component.

FIG. 2 illustrates a composite of the present disclosure functioning as backside or tray 22 in a tibial component 24. The tibial component 24 includes the tray 22 and an articulating component 28. The tray 22 has a fixation surface 26 defined thereon. The articulating component 28 has a polymeric bearing or articulating surface 30 defined thereon The tray 22 can be attached to the articulating component 28 in any number of well known techniques, e.g. screwed. In another embodiment, the tray 22 can be a composite layer integrally attached to the articulating component 28 via, for example, compression molding. As discussed above, the articulating surface 30 serves as a surface for an anatomical structure, or a prosthetic component, to articulate upon. A bone (not shown), or other anatomical structure, may be secured to the fixation surface 26 via one or more screws or via a cement.

Examples of making composites:

Example I

Coating: Mix 35 ml of 15% cold-water soluble grade of PVA (Sigma) with 14.2 g of hydroxyapatite powder (Aldrich)
Drying: At 50° C. overnight
Grinding: With mortar and pestle
Sieving: 60 Mesh sieve
Mixing: 13.0 gram of PVA-coated HA with 16.0 gram of GUR 1020 in Turbular mixer
Compression Molding: Heat-up rate of 10° F./min.-20° F./min., Melt temperature 350° F.-425° F., pressure 500 psi-2,000 psi, soak time 10 minutes-30 minutes, cooldown at 2° F./min.-5° F./min.

Example II

Coating: Mix 46 ml of 10% cold-water soluble grade of PVA with 14.2 g of HA powder
Filtering: 0.5 micron-pore funnel filter
Drying: At 50° C. overnight
Mixing: 12.0 gram of PVA-coated HA with 16.0 gram of GUR 1020 in Turbular mixer
Compression Molding: Same as Example I

Example III

Preparation of Polyvinyl Alcohol—Coated Hydroxyapatite (i) 10% PVA solution was prepared by dissolving 3.2 gram of PVA (75-80% degree of hydrolysis, molecular weight 30,000-70,000 Dalton) in 32 ml of cold R.O. water,
(ii) Hand mixing 14.2 gram of hydroxyapatite (reagent grade, Aldrich) with 32 ml of 10% PVA solution,
(iii) Dry the slurry in vacuum oven overnight at 50°-60° C.,
(iv) Crush coated powder with a mortar and pestle.
Consolidation of HA-Reinforced UHMWPE:
(i) Mixing PVA—coated hydroxyapatite with 16.0 gram of GUR 1020 (Ticona) in Turbular mixer,
(ii) Compression mold the mixture with melt soak temperature between 370° F. and 420° F. pressure between 800 and 1500 psi, duration between 10 and 30 minutes.
Comparison of UHMWPE, HA/UHMWPE and PVA-Coated HA/UHMWPE:

|  | UHMWPE | HA/UHMWPE | PVA-HA/UHMWPE |
|---|---|---|---|
| Hardness, D | 62 | 68 | 74 |
| Elastic Modulus, psi | 100,000 | 159,000 | 194,000 |
| Tensile Strength*, ksi | 6.0 | 2.1 | 2.8 |
| Elongation at Break | 397% | 3.5% | 3.1% |

*Tensile data were generated using ASTM D 638 Type V test specimens; generated at 0.6"/minute.

Figure 3:
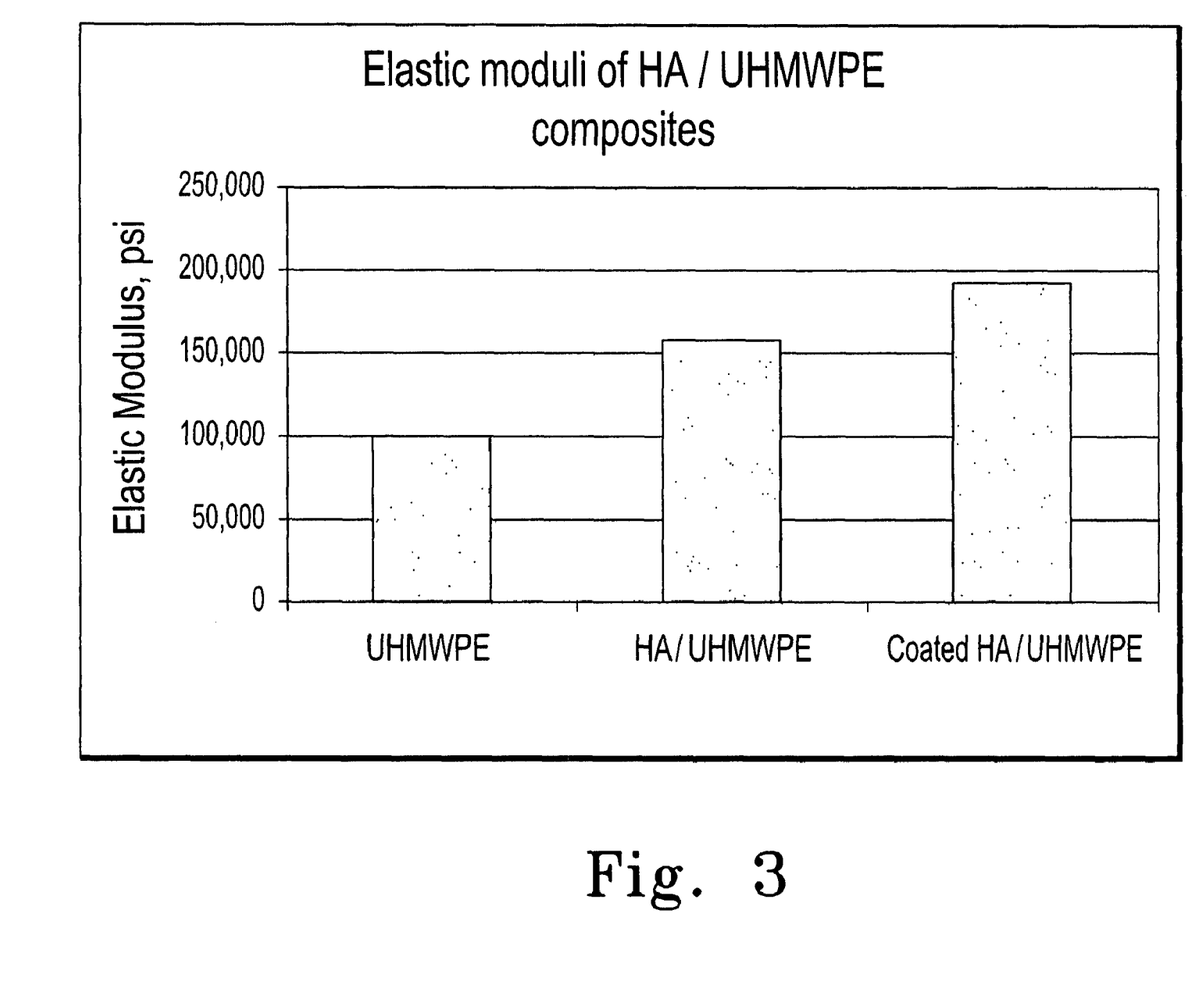
FIG. 3 is a graphical representation of the elastic modulus of several compositions.
Figure 4:
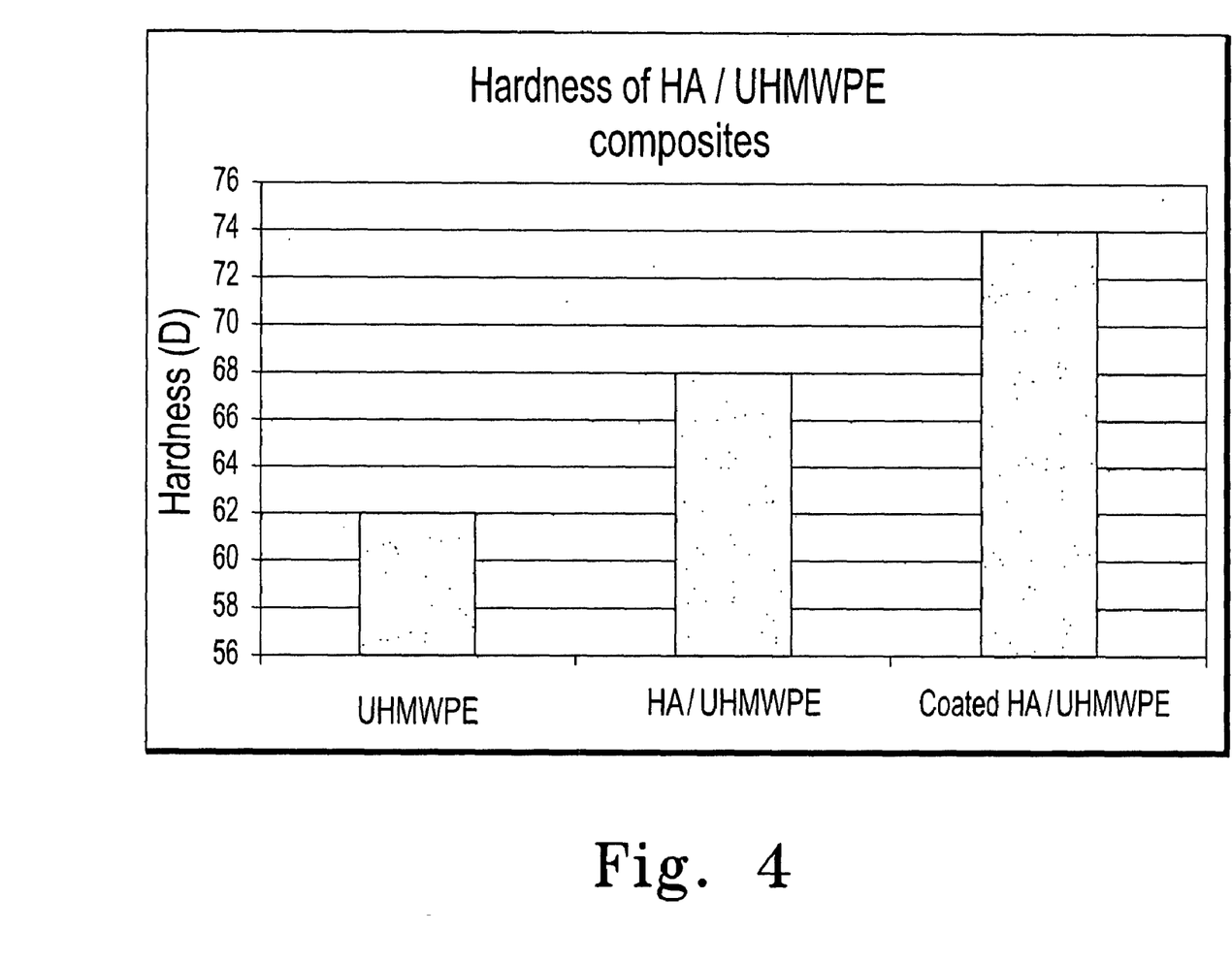
FIG. 4 is a graphical representation of the hardness of several compositions.

Note that graphic illustrations of the above elastic moduli and hardness results are shown in FIGS. 3 and 4. Also note that the examination of molded plaques showed that the PVA-coated HA/UHMWPE composite has improved HA dispersion in comparison with that of HA/UHMWPE composite. In addition, filtering the HA/PVA solution slurry before drying enhances HA dispersion in UHMWPE.

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected.

The invention claimed is:

1. A substance for implanting into the body of an animal, comprising:
a composite that includes discrete units of a polymer-coated ceramic substance disposed in a medical grade biocompatible polymeric material that includes a medical grade polyethylene, wherein the polymer coating material includes a poly(vinyl alcohol).

2. The substance of claim 1, wherein:
the ceramic substance includes one or more of the following, oxides, nitrides, borides, carbides, silicides, sulfides, aluminides, berylides, phosphides, antimonides, and arsenides.

3. The substance of claim 1, wherein:
the ceramic substance includes one or more of the following, hydroxyapatite, calcium phosphate, calcium carbonate, calcium sulfate, bioglass, zirconium oxide, barium sulfate, and titanium oxide.

4. The substance of claim 1, wherein:
the biocompatible polymer further includes one or more of the following, polyesters, polyacrylates, nylon, polycarbonates, and polyolefins.

5. The substance of claim 1, wherein:
the biocompatible polymer includes UHMWPE.

6. The substance of claim 1, wherein:
the ceramic substance includes one or more of the following, ceramic particles, ceramic fibers, and ceramic whiskers.

7. The substance of claim 6, wherein:
the ceramic particles are one or more of the following, nanoparticles and microparticles.

8. The substance of claim 1, wherein:
the polymer coating material further includes polyethylene copolymers.

9. The substance of claim 1, further comprising:
a ceramic free polymeric material attached to the composite.

10. The substance of claim 9, wherein:
the ceramic free polymer is integrally attached to the composite.

11. The substance of claim 1, wherein:
the composite is configured as a tray of an implantable orthopedic device.

12. The substance of claim 1, wherein:
the composite is configured as a shell of modular implantable orthopedic device.

13. A implantable arrangement, comprising:
an orthopedic device having a component, wherein the component includes a composite made from polymer-coated discrete units of a ceramic substance disposed in a biocompatible polymeric material that includes polyethylene, wherein the polymer coating material is different from the biocompatible polymer and includes poly(vinyl alcohol).

14. The implantable orthopedic device of claim 13, wherein:
the ceramic substance includes hydroxyapatite particles and the biocompatible polymeric material includes UHMWPE.

* * * * *